United States Patent [19]

Resmer

[11] Patent Number: 5,232,733
[45] Date of Patent: Aug. 3, 1993

[54] LIQUID DRINK AND TUBE FOOD CONTAINING STABLE GUAR FLOUR

[76] Inventor: Paul Resmer, Köbingerbergstrasse 22, 8090 Wasserburg, Fed. Rep. of Germany

[21] Appl. No.: 678,364
[22] PCT Filed: Aug. 31, 1990
[86] PCT No.: PCT/EP90/01466
　§ 371 Date: Apr. 24, 1991
　§ 102(e) Date: Apr. 24, 1991
[87] PCT Pub. No.: WO91/03170
　PCT Pub. Date: Mar. 21, 1991

[30] Foreign Application Priority Data

Aug. 31, 1989 [DE] Fed. Rep. of Germany ....... 3928922

[51] Int. Cl.⁵ .................. A23L 1/0532; A23L 1/0526
[52] U.S. Cl. .................................... 426/590; 426/573; 426/575; 426/800; 426/801; 426/804
[58] Field of Search ............... 426/573, 575, 590, 800, 426/801, 804

[56] References Cited

U.S. PATENT DOCUMENTS 4,390,550  6/1983  Kahn et al. .

FOREIGN PATENT DOCUMENTS

WO86/05363  9/1986  France .
61-323831  10/1986  Japan .
1124335  9/1965  United Kingdom .
84-198108  6/1984  United Kingdom .
2147188A  5/1985  United Kingdom .

Primary Examiner—Carolyn Paden
Attorney, Agent, or Firm—Nixon, Hargrave, Devans & Doyle

[57] ABSTRACT

In a guar-flour-containing drink and tube food by adding sodium alginate and/or agar-agar a stabilizing is achieved and the precipitation of the hydrocolloid guar flour during storage prevented.

13 Claims, No Drawings

LIQUID DRINK AND TUBE FOOD CONTAINING STABLE GUAR FLOUR

BACKGROUND OF THE INVENTION

In the nutritional treatment of disturbances of carbohydrate metabolism, in particular Diabetes mellitus, the use of guar flour obtained from the fruits of the Indian bush bean is becoming of increasing importance. Due to the content of the hydrocolloid galactomannan, on intake of a preparation containing swollen guar flour a highly viscous thin film layer forms on the small intestinal mucosa, thereby reducing the absorption rate of nutrients. It is therefore possible by specific administration of preswollen guar flour before a meal to control and equalize the blood sugar level in the peak values of diabetically predisposed patients, cf. Lembcke, B. et al., "Hepato-gastroenterol", vol. 31, p. 183–186 (1984).

Apart from this effect, which can be explained mainly on the basis of its physical character, a number of further important nutritional physiological effects are known following the administration of guar flour, for instance inter alia a reduction of the cholesterol level in blood serum and inactivation of pancreatic amylase and thus reduced enzymatic attack on the carbohydrates of the food on passage through the intestines. As a thickening agent in the chyme it increases the viscosity and thus suppresses the appetite. It also regulates the intestinal peristalsis and thus has an excellent ballast function. Moreover, certain lipometabolic disturbances can be successfully treated with guar flour with a dosage of about 10–15 g daily.

Attempts to avoid the hitherto usual individual administrations of guar flour and the complicated preswelling thus necessary before each meal by making available a complete finished homogenized and sterilized tube and drink food already containing the hydrocolloid guar flour in addition to the necessary nutrient components have not so far met with any success. Although by adding the guar flour to a liquid nutrient mixture it was possible to reduce the absorption rate of the maltodextrin used here as carbohydrate source to such an extent that the glucose level dropped appreciably compared with a standard meal, it was found that in this previously made preparation the guar flour introduced agglomerated in storage after a relatively short time, i.e. after about 8–14 days to form relatively large agglomerates of about 3–5 mm diameter in the tube nutrient solutions, and even floated partially on the surface of the nutrient solution as a sort of cake. In the case of such drink solutions as well on storage gelatinous sago-like particles formed which then caused unpleasant feelings in the mouth on intake of the preparation. The agglomeration of the hydrocolloid in some cases reached an extent such that relatively large cohesive flat cakes were disposed in the nutrient solution which then could not be broken down even by intensive shaking of the bottle.

On attempts to achieve a stabilizing, to avoid the effects of the agglomeration described, by adding another additional hydrocolloid to the guar-flour-containing nutrient solution, it was found that even when using relatively high concentrations most known hydrocolloids did not lead to any improvement. Thus, although the addition of amidated pectin, apple pectin, carboxymethyl cellulose, furcellaran, carob seed flour, lambda-carrageen, methyl cellulose, rice flour, tragacanth gum and xanthene leads to a synergistically increased viscosity value of the preparation, it does not produce any stabilization of the guar flour. However, surprisingly a stabilization was achieved by adding sodium alginate and/or agar-agar.

SUMMARY OF THE INVENTION

Therefore, according to the invention the guar-flour-containing drink and tube food additionally contains sodium alginate in an amount range from 0.1 to 5 g and/or 0.25 to 2 g agar-agar per liter solution. The use of the sodium alginate prevents the precipitation of the guar flour hydrogel so that the aforementioned rice-grain or sago-like particles no longer precipitate and float on the nutrient solution during storage. The guar flour hydrocolloid remains uniform and distributed practically invisibly in the solution, which can also be stored for relatively long times.

DESCRIPTION OF THE PREFERRED EMBODIMENTS

In the various sodium alginate types, the ratio of guluronic acid to mannuronic acid in the side chains of the alginate has an influence not only on the viscosity properties but also on the stabilizing effect in the guar-flour-containing solution. It would appear that electrostatically repellent forces of the carboxyl groups of the alginate hydrocolloid present play a part here. Preferably suitable here are alginates having a guluronic acid content with respect to the mannuronic acid content which is approximately equal to the ratio of conventional alginate types in which the mannuronic acid content predominates.

Such a sodium alginate type is available commercially for example under the name SATIALGINE SG 500 from the company Sanofi Bio Industries GmbH, Dusseldorf.

It has also been found particularly advantageous to use agar-agar types obtained from algae, for example cracilaria red algae which are cultivated on fields, in contrast to those agar-agar types which are obtained from algae washed up on the coast. Agar-agar types obtained from algae cultivated on fields are available commercially for example under the name Aldagar TG 1 (Company O.Aldag, Hamburg).

The drink and tube nutrient solutions containing guar flour in accordance with the invention can be stabilized very well and even on storing for a longer period of at least 6 months do not exhibit any precipitation of a guar flour phase. Also, the sodium alginate further promotes dietetically valuable effects of the guar flour.

Since the repellent forces on the one hand can be cancelled out again partially by the carboxyl groups of the sodium alginate by cations such as Na+, Ca++, Mg++, etc. in the nutrient solution, and on the other hand a nutritionally and physiologically expediently made up dietetic must also contain Ca++ ions in a certain amount, for example 500–600 mg/1000 kcal, and other cations, it is possible to determine easily by preliminary test the particular optimum amount of the sodium alginate required to substantially cancel out again the mutually influencing effects.

In general, such an optimum for the sodium alginate lies in the range from about 1.0 to 2.5 g/l liquid food with an amount of 5 to 10 g guar flour per liter.

Below, two examples are given of stable liquid dietetic nutrient solutions containing guar flour and sodium alginate or agar-agar:

1. Diabetes diet, liquid

| Ingredients | Example 1 Drink solution in g/l | Example 2 Tube sol. in g/l |
| --- | --- | --- |
| 1. milk proteins | 50.0 | 50.0 |
| 2. vegetable fat (e.g. soybean oil) | 36.0 | 36.0 |
| 3. partially degradated corn starch | 110.0 | 110.0 |
| 4. sugar substitute sorbitol | 10.0 | 10.0 |
| 5. guar flour | 5.0 | 5.0 |
| 6. sodium alginate or | 1.2 | 2.0 |
| 7. agar-agar | 1.5 | 1.0 |
| 8. mineral salts | 7.1 | 7.1 |
| 9. trace elements (only Fe) | 0.028 | 0.083 |
| 10. vitamins | 0.17 | 0.17 |
| 11. sweetening mixture (Natreen ®) | 0.30 | — |
| 12. emulsifiers | 2.0 | 2.0 |
| 13. aromatics (nat./nat. (i.d.) | 4.0 | — |
| 14. antioxidant | 0.2 | 0.2 |
| 15. drinking water | 834.002 | 837.447 |
| Total: | 1060.000 g | 1060.000 g |

2. Reduction diet, liquid

| Ingredients: | Example 3 in g/l | Example 4 in g/l |
| --- | --- | --- |
| 1. milk proteins | 27.4 | 46.5 |
| 2. skimmed milk | 616.0 | — |
| 3. vegetable fat (soybean oil) | 9.6 | 9.6 |
| 4. maltodextrin DE 11-14 | 39.6 | 72.0 |
| 5. mineral salts | 3.6 | 3.6 |
| 6. guar flour | 6.0 | 6.0 |
| 7. sodium alginate or | 1.0 | 1.0 |
| 8. agar-agar | 1.5 | 1.0 |
| 9. emulsifiers | 1.0 | 1.0 |
| 10. vitamin mix | 0.56 | 0.56 |
| 11. sweetening mixture (Natreen ®) | 0.44 | 0.44 |
| 12. antioxidant | 0.12 | 0.12 |
| 13. iron (II) sulfate | 0.05 | 0.05 |
| 14. drinking water | 343.00 g | 895.00 g |
| Total: | 1050.00 g | 1037.00 g |

These recipes of examples 1 and 2 with 4187 kJ = 1000 kcal correspond to a nutrient composition of protein:-fat:carbohydrate = 20:32:48 energy %. Their stability behaviour is to be rated equally good.

The recipe of example 3 represents a lactose-containing reduction diet and the recipe of example 4 an extremely low-lactose liquid reduction diet. They have per 1000 ml 2345 kJ = 560 kcal. They correspond to a nutrient composition of protein:fat:carbohydrates = 29:19:52 energy %.

Like the nutrient solutions in case 1 "diabetes diet", both reduction diets in liquid form also exhibit an excellent long-time stability and uniform dispersion of the guar over a period of at least 6 months; experience has shown this to be however 10 to 12 months.

The preparation of the recipes of examples 1 to 4 can be carried out in simple manner employing the following method steps:

1. Preswelling of the guar flour

The guar flour necessary for the mixture is mixed with part of the milk protein used in the mixture and slowly stirred into part of the necessary mixture water (at 85° C.) and preswollen until a thick whitish gel of uniformly high viscosity has formed.

2. Basic mixture of the main nutrients

In another mixture container the salts, the alginate or agar-agar, the carbohydrates and the remaining proteins and the emulsifier are introduced slowly into the container and mixed with a further part of the necessary mixture water (at about 60° C.) and stirred until homogeneous and free from lumps).

3. Uniting the basic mixture with the preswelling phase

After preparation of the two aforementioned phases they are united by means of a suitable conveying pump in a tank with continuous circulation. The temperature of the mixture is 70° C.

4. Preparation of the nonsterile complete mixture

The still required raw materials such as oil, vitamins, aromatic substances, sweeteners and possibly also trace elements, are introduced into the batch container using suitable emulsifying apparatuses. Unintentional beating in of air has a detrimental effect on the aforementioned ingredients and should always be avoided.

5. Presterilization and homogenization

To obtain adequate sterility, the still nonsterile product is immediately subjected to a presterilization by means of one of the known UHT methods at $135° +/- 1°$ C. with a heating time of 8–10 secs. A subsequent high-pressure homogenization gives the necessary fine dispersion of the fat droplets (about 0.5 $\mu$m to 3 $\mu$m) and thus a stable emulsion structure.

6. Filling and final sterilization

After an in-process control and determination of the important nutrient and other characteristics (for example dry mass, fat, protein, density, pH value and viscosity) the presterilized product is introduced into commercially usual sterile milk bottles (500 ml/200 ml), sealed and subjected to a final sterilization such that a commercially usual sterility sufficing during the minimum durability is achieved. When the quality control has been completed, extending to the foodstuff chemical, microbiological, technical and physical test features, and the products passed they can be delivered to the tray.

The product for tube feeding has a viscosity of about 70 cp (25° C.) and for the intended use has an adequate flowability (tube passage) of about 300 ml/h with a hydrostatic pressure head of about 1 m. The use and administration of this standardized guar-flour-containing balanced formula diet can be increased or otherwise adapted with the aid of a suitable nutrient pump.

In the aromatized drinking variants the product viscosity is of secondary importance; however, the solutions according to 1, 3 and 4 do have a viscosity very suitable for oral intake and promoting a good sensorial overall impression.

After storage for 6 months all the preparations were still stable.

I claim:

1. Liquid and stable drink and tube food comprising stable guar flour and an amount of sodium alginate sufficient to avoid agglomeration of said guar flour, said amount of sodium alginate being in the range of 0.1 to 5 g per liter.

2. Drink and tube food according to claim 1, wherein said amount of sodium alginate is in the range of 1.0-2.5 g per liter.

3. Drink and tube food according to claim 2 characterized by a content of swollen guar flour in an amount of 5 to 10 g per liter.

4. Drink and tube food according to claim 2 characterized by a sodium alginate having a content of guluronic acid radicals in the molecule approximately equal in magnitude to that of the mannuronic acid radicals.

5. Drink and food tube according to claim 2 wherein the agar-agar is obtained from red algae cultivated on algae fields.

6. Drink and tube food according to claim 1, utilizing a content of swollen guar flour in an amount of 5 to 10 g per liter.

7. Drink and tube food according to claim 6 characterized by a sodium alginate having a content of guluronic acid radicals in the molecule approximately equal in magnitude to that of the mannuronic acid radicals.

8. Drink and food tube according to claim 6 wherein the agar-agar is obtained from red algae cultivated on algae fields.

9. Drink and tube food according to claim 1, wherein said sodium alginate includes an approximately equal ratio of guluronic acid radicals to mannuronic acid radicals.

10. Drink and food tube according to claim 9 wherein the agar-agar is obtained from red algae cultivated on algae fields.

11. Liquid and stable drink and tube food comprising guar flour and an amount of agar-agar sufficient to avoid agglomeration of said guar flour, said amount of agar/agar being in the range of 0.25 to 2 g per liter.

12. Drink and tube food according to claim 11 wherein said agar-agar is obtained from cultivated red algae.

13. Drink and tube food according to claim 11 utilizing a content of swollen guar flour in an amount of 5 to 10 g per liter.

* * * * *